(12) United States Patent
Brahm

(10) Patent No.: US 10,905,798 B1
(45) Date of Patent: Feb. 2, 2021

(54) METHODS AND COMPOSITIONS FOR THE REPAIR AND REPLACEMENT OF CONNECTIVE TISSUE

(71) Applicant: BioDlogics, LLC, Cordova, TN (US)

(72) Inventor: Timothy R. Brahm, Germantown, TN (US)

(73) Assignee: BioDlogics, LLC, Cordova, TN (US)

( * ) Notice: Subject to any disclaimer, the term of this patent is extended or adjusted under 35 U.S.C. 154(b) by 110 days.

(21) Appl. No.: 16/386,453

(22) Filed: Apr. 17, 2019

Related U.S. Application Data

(62) Division of application No. 14/929,470, filed on Nov. 2, 2015, now Pat. No. 10,265,438.

(60) Provisional application No. 62/074,238, filed on Nov. 3, 2014.

(51) Int. Cl.
    *A61F 2/08*     (2006.01)
    *A61L 27/36*     (2006.01)
    *A61L 27/54*     (2006.01)
    *A61F 2/30*     (2006.01)
    *A61L 27/52*     (2006.01)
    *A61K 35/50*     (2015.01)

(52) U.S. Cl.
    CPC ............ *A61L 27/3604* (2013.01); *A61F 2/08* (2013.01); *A61F 2/30756* (2013.01); *A61L 27/3654* (2013.01); *A61L 27/3662* (2013.01); *A61L 27/3687* (2013.01); *A61L 27/52* (2013.01); *A61L 27/54* (2013.01); *A61F 2210/0076* (2013.01); *A61K 35/50* (2013.01); *A61L 2430/06* (2013.01); *A61L 2430/10* (2013.01)

(58) Field of Classification Search
    CPC ............ A61L 27/3654; A61L 27/3662; A61L 27/3843; A61L 27/3645; A61F 2/08
    See application file for complete search history.

(56) References Cited

U.S. PATENT DOCUMENTS

| | | | |
|---|---|---|---|
| 3,409,016 A | 11/1968 | Foley | |
| 4,120,649 A | 10/1978 | Schechter | |
| 4,361,552 A | 11/1982 | Baur | |
| 4,674,488 A | 6/1987 | Nashef et al. | |
| 4,894,063 A | 1/1990 | Nashef | |
| 5,036,056 A | 7/1991 | Kludas | |
| 5,607,590 A | 3/1997 | Shimizu | |
| 5,612,028 A | 3/1997 | Sackier et al. | |
| 5,618,312 A | 4/1997 | Yui et al. | |
| 6,152,142 A | 11/2000 | Tseng | |
| 6,254,637 B1 | 7/2001 | Lee et al. | |
| 6,326,019 B1 | 12/2001 | Tseng | |
| 7,494,802 B2 | 2/2009 | Tseng et al. | |
| 7,727,550 B2 | 6/2010 | Siegal et al. | |
| 7,871,646 B2 | 1/2011 | Ghinelli | |
| 8,071,135 B2 | 12/2011 | Liu et al. | |
| 8,153,162 B2 | 4/2012 | Tseng et al. | |
| 8,182,840 B2 | 5/2012 | Tseng et al. | |
| 8,182,841 B2 | 5/2012 | Tseng et al. | |
| 8,187,639 B2 | 5/2012 | Tseng et al. | |
| 8,932,805 B1 | 1/2015 | Brahm | |
| 8,956,862 B2 | 2/2015 | Pal et al. | |
| 8,961,617 B2 * | 2/2015 | Young | A61F 2/02 623/23.72 |
| 9,358,320 B2 * | 6/2016 | Samaniego | A61L 26/0095 |
| 10,265,438 B1 * | 4/2019 | Brahm | A61F 2/08 |
| 10,271,942 B2 * | 4/2019 | Tokish | A61L 27/3604 |
| 10,314,688 B2 * | 6/2019 | Shepard | A61L 27/3886 |
| 10,632,155 B2 * | 4/2020 | Tseng | A61P 27/02 |
| 2001/0053839 A1 | 12/2001 | Noishiki et al. | |
| 2003/0054331 A1 | 3/2003 | Fraser et al. | |
| 2003/0187515 A1 | 10/2003 | Hariri et al. | |
| 2003/0225355 A1 | 12/2003 | Butler | |
| 2004/0048796 A1 * | 3/2004 | Hariri | A61P 13/02 424/423 |
| 2004/0057938 A1 | 3/2004 | Ghinelli | |
| 2004/0170663 A1 | 9/2004 | Wang et al. | |
| 2004/0267362 A1 * | 12/2004 | Hwang | A61F 2/08 623/13.15 |
| 2005/0203636 A1 | 9/2005 | McFetridge | |
| 2006/0134050 A1 * | 6/2006 | Griffith | A61K 35/12 424/70.16 |
| 2007/0021762 A1 | 1/2007 | Liu et al. | |
| 2007/0031471 A1 | 2/2007 | Peyman | |
| 2007/0038298 A1 | 2/2007 | Sulner et al. | |
| 2007/0292401 A1 | 12/2007 | Harmon et al. | |
| 2008/0044848 A1 | 2/2008 | Heidaran | |
| 2008/0046095 A1 | 2/2008 | Daniel | |
| 2008/0131522 A1 | 6/2008 | Liu et al. | |
| 2008/0193554 A1 * | 8/2008 | Dua | A61L 31/005 424/558 |

(Continued)

FOREIGN PATENT DOCUMENTS

| | | |
|---|---|---|
| EP | 0781564 A2 | 7/1997 |
| EP | 0285370 B2 | 12/2002 |

(Continued)

OTHER PUBLICATIONS

Avanzi, et al., "Susceptibility of human placenta derived mesenchymal stromal/stem cells to human herpes virus infection", PLOS One, vol. 8, No. 8 (Aug. 2013), pp. 1-14.

Brooke et al., "Manufacturing of human placenta-derived mesenchymal stem cells for clinical trials", British Journal of Haematology, vol. 144 (2008), pp. 571-579.

Fuller, et al., "Stem cells", Clinical Applications of Cryobiology, (2000), pp. 127-134.

Gavin, "Histopathology of "fresh" human aortic valve allografts", Thorax, vol. 28 (1973), pp. 482-487.

Haimov-Kochman et al. "Modification of the standard trizol-based technique improves the integrity of RNA isolated from RNase-rich placental tissue", Clinical Chemistry, vol. 52, No. 1 (2006), pp. 159-160.

(Continued)

*Primary Examiner* — Seema Mathew
(74) *Attorney, Agent, or Firm* — Barnes & Thornburg LLP

(57) ABSTRACT

A biological construct for the repair and replacement of damaged connective tissue is provided. Methods of repairing or otherwise replacing connective tissue are also provided.

11 Claims, No Drawings

(56) References Cited

U.S. PATENT DOCUMENTS

| | | |
|---|---|---|
| 2008/0274184 A1 | 11/2008 | Hunt |
| 2009/0208551 A1 | 8/2009 | Kim et al. |
| 2010/0080840 A1 | 4/2010 | Cho et al. |
| 2010/0104539 A1 | 4/2010 | Daniel et al. |
| 2010/0106233 A1 | 4/2010 | Grant et al. |
| 2010/0120149 A1* | 5/2010 | Kim ............... A61K 35/28 435/396 |
| 2011/0129520 A1 | 6/2011 | Bogdansky et al. |
| 2011/0189301 A1 | 8/2011 | Yang et al. |
| 2011/0206776 A1 | 8/2011 | Tom et al. |
| 2012/0009644 A1 | 1/2012 | Hamby et al. |
| 2012/0009679 A1 | 1/2012 | Hamby et al. |
| 2012/0010727 A1* | 1/2012 | Young ............ A61L 27/3641 623/23.72 |
| 2012/0035744 A1 | 2/2012 | Young et al. |
| 2012/0078378 A1 | 3/2012 | Daniel et al. |
| 2012/0083900 A1 | 4/2012 | Samaniego et al. |
| 2012/0141595 A1* | 6/2012 | Tseng ............... A61K 35/44 424/583 |
| 2013/0287741 A1 | 10/2013 | Stilwell et al. |
| 2014/0017280 A1 | 1/2014 | Daniel et al. |
| 2014/0037598 A1 | 2/2014 | Jansen et al. |
| 2014/0050788 A1* | 2/2014 | Daniel ............ A61L 26/0057 424/489 |
| 2014/0052247 A1 | 2/2014 | Daniel et al. |
| 2014/0052274 A1* | 2/2014 | Koob ............... A61K 35/50 623/23.73 |
| 2014/0058496 A1 | 2/2014 | Tranquillo et al. |
| 2014/0067058 A1* | 3/2014 | Koob ............... A61L 27/44 623/4.1 |
| 2014/0323322 A1 | 10/2014 | Asher |
| 2016/0143720 A1* | 5/2016 | Matheny ............ A61F 2/02 606/151 |
| 2016/0250385 A1 | 9/2016 | Cullen et al. |
| 2016/0324902 A1* | 11/2016 | Tseng ............ A61L 27/3886 |
| 2017/0203004 A1* | 7/2017 | Murphy ............ A61L 27/227 |
| 2018/0155678 A1* | 6/2018 | Francis ............ C12N 5/0068 |
| 2019/0358366 A1* | 11/2019 | Zawko ............ A61L 27/3633 |

FOREIGN PATENT DOCUMENTS

| | | |
|---|---|---|
| WO | 2006094247 A2 | 9/2006 |
| WO | 2009044408 A1 | 4/2009 |
| WO | 2009052132 A1 | 4/2009 |
| WO | 2009132186 A1 | 10/2009 |
| WO | 2012003377 A2 | 1/2012 |
| WO | 2012112417 A2 | 8/2012 |
| WO | 2012112441 A1 | 8/2012 |

OTHER PUBLICATIONS

Jaattela, et al., "Demonstration of tumor necrosis factor in human amniotic fluids and supernatants of placental and decidual tissues", Laboratory Investigation, vol. 58, No. 1 (1998), pp. 48-52.

Kagan, "The skin bank", Chapter 15 in Total Burn Care (2012), pp. 199-208.

Liu, et al., "The use of type I and type II injectable human collagen for dermal fill: 10 years of clinical experience in China", Seminars in Plastic Surgery, vol. 19, No. 3 (2005), pp. 241-250.

Parolini, et al., "Concise review: Isolation and characterization of cells from human term placenta: Outcome of the first international workshop on placenta derived stem cells", Stem Cells, vol. 26 (2008), pp. 300-311.

Sabapathy, et al., "Long-term cultured human term placenta-derived mesenchymal stem cells of maternal original displays plasticity", Stem Cells International, vol. 2012 (2012), pp. 1-11.

Scheffer et al., "Amniotic membrane transplantation with or without limbal allografts for corneal surface reconstruction in patients with limbal stem cell deficiency", Archives of Opthalmology, vol. 116, No. 4 (1998), pp. 431-441.

Federal Register, "Human cells, tissues and cellular and tissue-based products; establishment registration and listing", Federal Register, vol. 66, No. 13 (Jan. 19, 2001), pp. 5447-5469.

American Association of Tissue Banks, "Standards for Tissue Banking", 13th edition, published Feb. 29, 2012, p. 58.

Court Case No. CV-15-00095-PHX-SRB, "Order Staying all proceedings pending reexamination of U.S. Pat. No. 8,932,805", *Amnio Technology, LLC* v. *BioDlogics, LLC*, filed Sep. 30, 2015.

Electronic Code of Federal Regulations, § 1271.220 "Processing and process controls", downloaded Nov. 18, 2015.

\* cited by examiner

METHODS AND COMPOSITIONS FOR THE REPAIR AND REPLACEMENT OF CONNECTIVE TISSUE

CROSS-REFERENCE TO RELATED APPLICATIONS

The present application is a divisional of U.S. application Ser. No. 14/929,470, filed Nov. 2, 2015, now U.S. Pat. No. 10,265,438, which claims the benefit of U.S. provisional Application No. 62/074,238 filed Nov. 3, 2014, the contents of each are incorporated herein by reference in their entirety.

FIELD OF THE INVENTION

The present invention is directed to a biological construct composed of aseptically recovered human birth tissue, as well as methods of using the same to repair or otherwise replace connective tissue.

BACKGROUND OF THE INVENTION

Connective tissue (e.g., tendons, ligaments, cartilage) is prone to damage due to the stress imposed on it through physical activity such as sports and exercise. Such damage is commonly manifested as tears, ruptures, or other similar defects. The most common methods of repairing such defects in connective tissue such as cartilage include osteochondral autograft transfer system (OATS) and mosaicplasty procedures. Such cartilage transfer procedures involve moving healthy cartilage from an area of the knee that is non-weight bearing to a damaged cartilage area of the knee. In mosaicplasty, plugs of healthy cartilage and bone are taken from a healthy cartilage area and moved to replace the damaged cartilage area of the knee. Multiple tiny plugs are used and once embedded, resembles a mosaic. With the OATS procedure, the plugs are typically large. Therefore, the surgeon only needs to move one or two plugs of healthy cartilage and bone to the damaged area of the knee. OATS is used with patients with minimal cartilage damage, usually as a result of trauma, with available healthy cartilage for transfer. While such procedures are generally met with success in younger patients, complications such as post-operative bleeding, pain, swelling, deep vein thrombosis may arise in addition to the requirement of maintaining a rigorous physical therapy routine. Also, widespread cartilage damage cannot be treated with such procedures as there is insufficient healthy cartilage available in the patient. Still further, these techniques result in open harvest sites that must heal on their own or be filled with a backfill plug.

Thus, there remains a need in the art for safe and effective materials and techniques to aid in the repair or replacement of damaged connective tissue such as cartilage.

SUMMARY OF THE INVENTION

According to one aspect, a multi-layer biological construct for repairing or replacing a damaged connective tissue is provided. According to one embodiment, the biological construct includes at least one bottom or basement layer that includes: (i) at least one amniotic membrane, at least one chorionic membrane, or at least one of both an amniotic and chorionic membrane that is/are processed in a manner that includes treatment with at least one alcohol composition such as, for example, 90% to about 100% ethanol; or (ii) at least one cross-linked amniotic membrane, at least one cross-linked chorionic membrane, or at least one of both a cross-linked amniotic and cross-linked chorionic membrane that is/are processed in a manner that includes treatment with a cross-linking solution such as, for example, glutaraldehyde.

According to one embodiment, the biological construct includes at least one top layer that includes: (i) at least one amniotic membrane, at least one chorionic membrane, or at least one of both an amniotic and chorionic membrane that is/are processed in a manner that includes treatment with at least one alcohol composition such as, for example, 90% to about 100% ethanol; or (ii) at least one cross-linked amniotic membrane, at least one cross-linked chorionic membrane, or at least one of both a cross-linked amniotic and cross-linked chorionic membrane that is/are processed in a manner that includes treatment with a cross-linking solution such as, for example, glutaraldehyde.

According to one embodiment, the biological construct includes at least one morselized layer. The at least one morselized layer includes at least one morselized human birth tissue component. The at least one morselized human birth tissue component may be at least one component of the placental organ such as placental globe, umbilical cord tissue, umbilical cord blood, amniotic membrane, amniotic fluid, chorionic membrane, Wharton's jelly, placental globe, placental gelatin, placental fluid, placental cells, or placental extracellular matrix. According to one embodiment, the morselized layer includes at least one morselized amniotic membrane, at least one morselized chorionic membrane, or at least one of both morselized amniotic and chorionic membrane. According to one embodiment, the morselized layer is flowable.

According to one embodiment, each layer is secured to a neighboring layer via a tissue glue or tissue adhesive. According to one embodiment, the alcohol composition used to treat the top or bottom layer comprises from about 90% to about 100% ethanol. According to one embodiment, the cross-linking solution used to treat the top or bottom layer comprises from about 0.01% to about 3% glutaraldehyde.

According to another aspect, a method of repairing or replacing a damaged connective tissue is provided. The method includes the steps of providing a biological construct as provided herein and contacting the damaged connective tissue with the biological construct. According to one embodiment, the damaged connective tissue is a tendon, ligament, or cartilage. According to one embodiment, the cartilage is located in or around an ankle, foot, knee, shoulder or elbow. According to one embodiment, the step of contacting the damaged connective tissue includes implanting the construct into a cavity created as a result of a surgical procedure. According to one embodiment, the surgical procedure is OATS or mosaicplasty.

According to another aspect, a kit is provided that includes at least one biological construct as provided herein and at least one set of instructions.

DETAILED DESCRIPTION OF THE INVENTION

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the present disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

As used in the specification, and in the appended claims, the words "optional" or "optionally" mean that the subsequently described event or circumstance can or cannot occur.

As used herein, the term "connective tissue" refers to a tendon, ligament, cartilage, or a combination thereof.

As used herein, the term "human birth tissue" includes, but is not limited to, elements of the placental organ such as, for example, the placental globe, the umbilical cord, the umbilical cord blood, the chorionic membrane, the amniotic membrane, the amniotic fluid, and other placental gelatins, fluids, cells and extracellular material obtained from a seronegative, healthy human.

As used herein, the term "placental tissue components" include amniotic membrane, chorionic membrane, Wharton's jelly, umbilical cord tissue, placental globe, other gelatins, other cells and extracellular matrix from human birth tissue.

As used herein, the term "membrane" refers to an amniotic membrane, a chorionic membrane, or both a chorionic and an amniotic membrane.

As used herein, the term "flowable" refers to the capability of flowing or being flowed.

As used herein, "morselization" (or "morselized") refers to grinding up to particle form.

The present disclosure generally relates to a biological construct for the repair and replacement of damaged connective tissue. The biological construct demonstrates strength and biocompatibility superior to that of existing synthetic implants and is comparable to an autologous material. Thus, the risk of rejection and subsequent complications (infections, inflammation, pain, shrinkage, etc.) are substantially reduced while eliminating the need to remove healthy connective tissue from elsewhere in the body. The present disclosure further relates to methods for aseptically processing human birth tissue to produce such biological constructs as well as methods of repairing or replacing damaged connective tissue.

According to one embodiment, the biological construct includes multiple layers of human birth tissue. Each human birth tissue layer is processed in a manner provided herein and then assembled to form a single construct. According to such an embodiment, the resulting multi-layer construct may be cut or otherwise sized to cover or fill an area of connective tissue injury.

According to one embodiment, the biological construct includes at least one bottom or basement layer that includes: (i) at least one amniotic membrane, at least one chorionic membrane, or at least one of both an amniotic and chorionic membrane that is/are processed in a manner that includes treatment with at least one alcohol composition such as, for example, 90% to about 100% ethanol; or (ii) at least one cross-linked amniotic membrane, at least one cross-linked chorionic membrane, or at least one of both a cross-linked amniotic and cross-linked chorionic membrane that is/are processed in a manner that includes treatment with a cross-linking solution such as, for example, glutaraldehyde. According to one embodiment, the biological construct includes more than one bottom layer as provided herein.

According to one embodiment, the biological construct includes at least one final or top layer that includes: (i) at least one amniotic membrane, at least one chorionic membrane, or at least one of both an amniotic and chorionic membrane that is/are processed in a manner that includes treatment with at least one alcohol composition such as, for example, 90% to about 100% ethanol; or (ii) at least one cross-linked amniotic membrane, at least one cross-linked chorionic membrane, or at least one of both a cross-linked amniotic and cross-linked chorionic membrane that is/are processed in a manner that includes treatment with a cross-linking solution such as, for example, glutaraldehyde. According to one embodiment, the biological construct includes more than one top layer as provided herein.

According to one embodiment, the biological construct includes at least one morselized layer. The morselized layer is formed by subjecting at least one human birth tissue component to morselization. Tissue morselization may occur by any art-recognized method of tissue disruption, including, but not limited to: milling, blending, sonicating, homogenizing, micronizing, pulverizing, macerating, hand pressing, or a combination thereof. According to one embodiment, the human birth tissue components are subjected to cryogenic milling by methods commonly known in the art. In a preferred embodiment, the human birth tissue components is cryogenically milled in a CryoMill® (available from Retsch) for two cycles at a frequency 1/s of 25 Hz with a pre-cooling time of no more than about five minutes, a grinding time of no more than about two minutes, and an intermediate cooling time of no more than about five minutes. In another embodiment, a Freezer/Mill® available from SPEX SamplePrep, LLC may be used. After morselization, the milled human birth tissue can be retained and preserved until use in the biological construct provided herein.

According to one embodiment, the human birth tissue may be morselized or otherwise rendered into fine particulates. Particles may be micron or submicron size ranges. In one embodiment, particle sizes may range from 1 micron to 100 microns. In another embodiment, particle sizes may range from 10 nm to 100 nm. Particles must be of sufficient size to allow diffusion through skin.

According to one embodiment, the morselized layer comprises at least one morselized human birth tissue component. The at least one morselized human birth tissue component may be at least one component of the placental organ such as placental globe, umbilical cord tissue, umbilical cord blood, amniotic membrane, amniotic fluid, chorionic membrane, Wharton's jelly, placental globe, placental gelatin, placental fluid, placental cells, or placental extracellular matrix. According to one embodiment, the morselized layer includes at least one morselized amniotic membrane, at least one morselized chorionic membrane, or at least one of both morselized amniotic and chorionic membrane. According to one embodiment, at least one morselized layer as provided herein is included between each of the membrane layers of the multi-layer biological construct as provided herein.

According to one embodiment, the morselized layer may be formulated as a hydrogel. According to one embodiment, the hydrogel includes at least one hydrophilic polymer and water. According to one embodiment, the hydrogel includes one or more liquid or solid components to aid strength and biocompatibility of the construct. According to one embodiment, the hydrogel is flowable.

According to one embodiment, the morselized layer includes human birth tissue that is fresh, frozen prior to morselization, frozen after morselization, or formulated into a powder. According to one embodiment, the powder is formed from frozen and lyophilized human birth tissue material.

According to one embodiment, the biological construct as provided herein includes at least one basement layer, at least one top layer, and a morselized layer with each of the aforementioned three layers repeated at least two or more times to form a biological construct of at least six layers.

Each layer of the multi-layer biological construct as provided herein can be optionally secured to a neighboring layer by any variety of methods such that the layers are stabilized. According to a preferred embodiment, each layer is secured to a neighboring layer via a tissue glue or tissue adhesive. Such a tissue glue or tissue adhesive may be used alone or in combination with at least one morselized layer.

The biological construct as provided herein includes human birth tissue material. To obtain such material, potential human birth tissue donors providing informed consent are pre-screened during an examination of pre-natal medical records and blood test results. A comprehensive medical history and behavior risk assessment is obtained from the donor prior to donation incorporating U.S. Public Health Service guidelines. Discussions with the physician(s) and/or the donor mother are conducted to identify circumstances that may lead to the exclusion of the donor or donated tissue. Additionally, a physical exam is performed on the donor to determine whether there is evidence of high risk behavior or infection and to determine the overall general health of the donor.

Infectious disease testing of donor blood specimens is performed for each tissue donor on a specimen collected at the time of donation or within seven days prior to or after donation. Exemplary infectious disease testing includes, but is not limited to, antibodies to the human immunodeficiency virus, type 1 and type 2 (anti-HIV-1 and anti-HIV-2); nucleic acid test (NAT) for HIV-1; hepatitis B surface antigen (HBsAg); total antibodies to hepatitis B core antigen (anti-HBc—total, meaning IgG and IgM); antibodies to the hepatitis C virus (anti-HCV); NAT for HCV; antibodies to human T-lymphotropic virus type I and type II (anti-HTLV-1 and anti-HTLV-II); and syphilis (a non-treponemal or treponemal-specific assay may be performed).

Human birth tissue is preferably recovered from a full-term aseptic Cesarean delivery of a newborn. Alternatively, human birth tissue is recovered from a full-term vaginal delivery of a newborn. The placental organ, including the placental globe, umbilical cord, associated membranes (chorionic membrane and amniotic membrane), other gelatins, fluids, cells and extracellular matrix can be recovered from a seronegative, healthy human after the newborn is removed. The placental globe, umbilical cord, other gelatins, fluids, cells and extracellular matrix can be removed and discarded.

The membranes giving rise to the biological construct as described herein may be produced by processing human birth tissue according to the steps provided herein. Processing does not change the physical properties of the resulting membrane so as to yield the membrane tissue unacceptable for clinical use. Instruments, solutions, and supplies coming into contact with tissue during the processing of the placental tissue are sterile. All surfaces coming in contact with tissue intended for transplant are either sterile or draped using aseptic technique.

Throughout processing, the orientation of the particular membrane is identified to ensure that in use the correct side of the membrane is placed on the wound. Either the fetal side or the maternal side of the membrane may be used depending upon the specific use or procedure that is being performed. The recovered amniotic membrane, chorionic membrane, or both amniotic and chorionic membrane may be initially stored in a sterile saline solution at a temperature between about 1° C. to about 10° C. for a period of up to about 120 hours prior to further processing. According to one embodiment, the sterile saline solution comprises from about 0.09% to about 20% NaCl.

According to one embodiment, the biological construct includes at least one top or basement layer that is prepared by the following steps:
  agitating the basin to liberate excess blood and fluids from the membrane;
  rinsing the membrane with a sterile saline solution;
  covering the membrane with a substrate on both the fetal membrane side and the maternal membrane side;
  optionally, rinsing the membrane with a sterile saline solution;
  optionally, soaking the membrane in a sterile saline solution;
  immersing the membrane in an alcohol composition for a period of from about 24 hours to about 384 hours;
  removing the substrate from both the fetal membrane side and the maternal membrane side;
  spreading the membrane on a flat, dry and sterile surface;
  allowing the membrane to air dry completely at ambient temperature for a period of up to three hours;
  cutting the membrane to a predetermined size to form at least one top or basement layer of the multi-layer construct.

According to one embodiment, the biological construct includes at least one top or basement layer that is prepared by the following steps:
  agitating the basin to liberate excess blood and fluids from the membrane;
  rinsing the membrane with a sterile saline solution;
  covering the membrane with a substrate on both the fetal membrane side and the maternal membrane side;
  immersing the membrane in a preservative solution for a period of up to about 20 minutes, wherein the preservative solution comprises from about 0.01% to about 3% of a cross-linking solution such as, for example, glutaraldehyde;
  optionally, rinsing the membrane with a sterile saline solution;
  optionally, soaking the membrane in a sterile saline solution;
  immersing the membrane in an alcohol composition for a period of from about 24 hours to about 384 hours;
  removing the substrate from both the fetal membrane side and the maternal membrane side;
  spreading the membrane on a flat, dry and sterile surface;
  allowing the membrane to air dry completely at ambient temperature for a period of up to three hours;
  cutting the membrane to a predetermined size to form at least one top or basement layer of the multi-layer construct.

According to one embodiment, the material for the at least one morselized layer of the biological construct may be prepared according to the following steps:
  recovering placental tissue components and amniotic fluid from a seronegative, healthy human via cesarean section or vaginal delivery;
  subjecting the placental tissue components to cryopreservation;
  morselizing the cryopreserved placental tissue components;
  homogenizing the morselized placental tissue components in a tissue suspension solution to form a tissue suspension;
  homogenizing the tissue suspension with an amniotic fluid composition to form a bulk tissue product; and
  cryofreezing the bulk tissue product to form the material for the at least one morselized layer material.

According to another embodiment, the material for the at least one morselized layer of the biological construct may be prepared according to the following steps:

recovering placental tissue components and amniotic fluid from a seronegative, healthy human via cesarean section or vaginal delivery;

subjecting the placental tissue components to cryopreservation;

morselizing the cryopreserved placental tissue components;

homogenizing the morselized placental tissue components in a tissue suspension solution to form a tissue suspension;

cryofreezing the bulk tissue product to form the material for at least one morselized layer material.

The biological construct as provided herein can be terminally sterilized using irradiation. In one embodiment, an electron beam irradiation is applied in an amount up to about 45 kGy. The sterilized construct may be stored for up to typically about two years from the date of processing. In one embodiment, the construct may be stored under proper conditions for as much as about five years following processing. According to a preferred embodiment, the construct may be stored under proper conditions for two years following processing. The sterilized construct may be stored in any container suitable for long-term storage. Preferably, the construct is stored in a sterile double peel-pouch package.

According to one embodiment, the biological construct as provided herein can be used to repair or replace connective tissue throughout the human body. The biological construct can be contacted with connective tissue in any medically-acceptable manner that tends to facilitate healing of a defect in or on the connective tissue. According to one embodiment, the biological construct can be used to repair an injury to cartilage in a joint such as, for example, the knee, finger, shoulder, foot, or ankle.

According to a particular embodiment, the biological construct as provided herein is particular suitable as a surrogate for autologous connective tissue that is typically used in cartilage repair procedures. For example, an OATS or mosaicplasty procedure typically entails the removal of a cartilage core or plug to form a cavity as a result of removing an area of cartilage damage. Instead of filing the plug with healthy, autologous material, a biological construct as provided herein may be used to fill in the cavity formed during an OATS or mosaicplasty procedure. According to one embodiment, the biological construct is a multi-layer construct as provided herein. According to such an embodiment, the multi-layer construct may be cut or otherwise shaped to fill the cavity. According to a preferred embodiment, the biological construct is positioned in the cavity such that the first, bottom layer(s) is/are placed at the bottom of the cavity with the top layer(s) closest to the skin of the patient. According to one embodiment, the multi-layer construct is provided to the surgical facility in a rounded or disc shape typical of the cavity size formed during OATS and mosaicplasty procedures. According to another embodiment, the multi-layer construct is provided to the surgical facility in individual layers such that the final construct is assembled by a medical professional at the time of surgery.

The biological construct can be secured into position via a variety of techniques well-known to those skilled in the art, including, but not limited to, tissue glue/adhesives (e.g., fibrin glue), sutures or staples. In certain embodiments, the biological construct can be held in place such that the biological construct assumes at least part of the biomechanical load normally associated with the connective tissue.

A kit for use by a medical professional is also provided. According to one embodiment, the kit includes one or more packaged biological constructs as provided herein. The kit may further include at least one set of instructions. The kit may further include a container adapted to accommodate and preserve the aforementioned components per applicable Food and Drug Administration guidelines. According to a particular embodiment, the kit includes one or more multi-layer biological constructs as provided herein. According to such an embodiment, the individual layers may be packaged together in a single unit ready for implantation. Alternatively, each layer may be packaged separately and assembled via the surgical professional at the time of surgery. According to one embodiment, the kit may include one or more components to aid the surgical professional in assembly and/or implantation including sutures or tissue glue/adhesive.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the invention are intended to be included with the scope of the appended claims.

I claim:

1. A method of repairing or replacing a damaged connective tissue, comprising the steps of:
   contacting the damaged connective tissue with a multi-layer biological construct, the multi-layer biological construct comprising
   at least one bottom layer;
   at least one top layer; and
   a flowable morselized layer formulated as a hydrogel and located between each of the bottom and top layers, the flowable morselized layer comprising amniotic fluid and at least one morselized human birth tissue component, and
   wherein each of the bottom layer and top layer comprise one of the following:
   at least one chemically dehydrated amniotic membrane, at least one chemically dehydrated chorionic membrane, at least one of both a chemically dehydrated amniotic and chemically dehydrated chorionic membrane, at least one cross-linked amniotic membrane, at least one cross-linked chorionic membrane, and at least one of both a cross-linked amniotic and cross-linked chorionic membrane.

2. The method of claim 1, wherein the damaged connective tissue is a tendon, ligament, or cartilage.

3. The method of claim 2, wherein the cartilage is located in or around an ankle, foot, knee, shoulder or elbow.

4. The method of claim 3, wherein the step of contacting the damaged connective tissue includes implanting the construct into a cavity created as a result of a surgical procedure.

5. The method of claim 4, wherein the surgical procedure is OATS or mosaicplasty.

6. The method of claim 1, wherein the morselized human birth tissue component comprises morselized amniotic membrane, morselized chorionic membrane, or both morselized amniotic and morselized chorionic membrane.

7. The method of claim 1, wherein each layer is secured to a neighboring layer via a tissue glue or tissue adhesive.

8. The method of claim 1, wherein hydrogel includes at least one hydrophilic polymer and water.

9. The method of claim 1, wherein the hydrogel includes one or more liquid or solid components to aid strength and biocompatibility of the construct.

10. The method of claim 1, wherein the hydrogel is flowable.

11. The method of claim 1, wherein the human birth tissue component is fresh, frozen prior to morselization, or frozen after morselization.

\* \* \* \* \*